United States Patent
Hahm

(10) Patent No.: US 9,587,000 B2
(45) Date of Patent: Mar. 7, 2017

(54) VP16-CREB FUSION GENE

(71) Applicant: Sung Ho Hahm, Cheongju-si (KR)

(72) Inventor: Sung Ho Hahm, Cheongju-si (KR)

(73) Assignee: Sung Ho Hahm, Cheongju-si (KR)

( * ) Notice: Subject to any disclaimer, the term of this patent is extended or adjusted under 35 U.S.C. 154(b) by 0 days.

(21) Appl. No.: 14/709,923

(22) Filed: May 12, 2015

(65) Prior Publication Data

US 2016/0115443 A1    Apr. 28, 2016

Related U.S. Application Data

(60) Provisional application No. 61/992,092, filed on May 12, 2014.

(51) Int. Cl.
| | |
|---|---|
| *C12N 5/16* | (2006.01) |
| *C07K 14/47* | (2006.01) |
| *C07K 16/00* | (2006.01) |

(52) U.S. Cl.
CPC .......... *C07K 14/47* (2013.01); *C07K 14/4705* (2013.01); *C07K 16/00* (2013.01); *C07K 2317/14* (2013.01); *C07K 2319/71* (2013.01); *C07K 2319/80* (2013.01); *C12N 2510/02* (2013.01)

(58) Field of Classification Search
None
See application file for complete search history.

(56) References Cited

U.S. PATENT DOCUMENTS

| | | | | |
|---|---|---|---|---|
| 6,773,920 B1* | 8/2004 | Dalby | ................ | A61K 48/0025 435/455 |
| 2004/0097454 A1* | 5/2004 | Reusch | ............. | C07K 14/4705 514/44 R |

* cited by examiner

*Primary Examiner* — Jim Ketter
(74) *Attorney, Agent, or Firm* — Joseph Hyosuk Kim; JHK Law

(57) ABSTRACT

The present application describes a cell that has integrated into its genome fusion molecule V16-CREB.

3 Claims, 10 Drawing Sheets

SEQUENCE LISTING

<160> NUMBER OF SEQ ID NOS: 12

<210> SEQ ID NO 1
<211> LENGTH: 1026
<212> TYPE: DNA
<213> ORGANISM: Artificial Sequence
<220> FEATURE:
<223> OTHER INFORMATION: VP16-CREB

<400> SEQUENCE: 1

```
atgaagctac tgtcttctat cgaacaagca tgcccaaaaa agaagagaaa ggtagatgaa      60
tttcctggga tctctactgc tcctccaacc gatgtcagcc tgggcgacga actccactta     120
gacggcgagg acgtggcgat ggcgcatgcc gacgcgctag acgatttcga tctggacatg     180 ttggggacg gggattcccc gggtccggga tctccagcga ttccgtcgac accacctact     240
ccctctccag cgatcgcctc ttcctgtaag gacttaaaaa gacttttctc cggaacacag     300
atttcaacta ttgcagaaag tgaagattca caggagtcag tggatagtgt aactgattcc     360
caaaagcgaa gggaaattct ttcaaggagg ccttcctaca ggaaaattt gaatgactta      420 tcttctgatg caccaggagt gccaaggatt gaagaagaga agtctgaaga ggagacttca     480
gcacctgcca tcaccactgt aacggtgcca actccaattt accaaactag cagtggacag     540
tatattgcca ttacccaggg aggagcaata cagctggcta acaatggtac cgatggggta     600
cagggcctgc aaacattaac catgaccaat gcagcagcca ctcagccggg tactaccatt     660
ctacagtatg cacagaccac tgatggacag cagatcttag tgcccagcaa ccaagttgtt     720
gttcaagctg cctctggaga cgtacaaaca taccagattc gcacagcacc cactagcact     780
attgcccctg gagttgttat ggcatcctcc ccagcacttc ctacacagcc tgctgaagaa     840
gcagcacgaa agagagaggt ccgtctaatg aagaacaggg aagcagctcg agagtgtcgt     900
agaaagaaga aagaatatgt gaaatgttta gaaacagag tggcagtgct tgaaaatcaa     960
aacaagacat tgattgagga gctaaagca cttaaggacc tttactgcca caatcagat    1020 gttaa                                                                 1026
```

<210> SEQ ID NO 2
<211> LENGTH: 210
<212> TYPE: DNA
<213> ORGANISM: Artificial Sequence
<220> FEATURE:
<223> OTHER INFORMATION: fusion sequence comprising 33 nucleotides sequence from GAL4, SV40 large T nuclear targeting sequence, and herpes simplex virus VP16 transactivation domain sequence

<400> SEQUENCE: 2

```
atgaagctac tgtcttctat cgaacaagca tgcccaaaaa agaagagaaa ggtagatgaa      60
tttcctggga tctctactgc tcctccaacc gatgtcagcc tgggcgacga actccactta     120
gacggcgagg acgtggcgat ggcgcatgcc gacgcgctag acgatttcga tctggacatg     180
```

```
ttgggggacg gggattcccc gggtccggga                                      210
```

```
<210> SEQ ID NO 3
<211> LENGTH: 39
<212> TYPE: DNA
<213> ORGANISM: Artificial Sequence
<220> FEATURE:
<223> OTHER INFORMATION: IgA linker

<400> SEQUENCE: 3
tctccagcga ttccgtcgac accacctact ccctctcca                             39

<210> SEQ ID NO 4
<211> LENGTH: 13
<212> TYPE: PRT
<213> ORGANISM: Artificial Sequence
<220> FEATURE:
<223> OTHER INFORMATION: amino acid sequence of IgA linker

<400> SEQUENCE: 4

Ser Pro Ala Ile Pro Ser Thr Pro Pro Thr Pro Ser Pro
1               5                   10

<210> SEQ ID NO 5
<211> LENGTH: 762
<212> TYPE: DNA
<213> ORGANISM: Artificial Sequence
<220> FEATURE:
<223> OTHER INFORMATION: DNA encoding CREB DNA binding domain sequence

<400> SEQUENCE: 5
tcttcctgta aggacttaaa aagactttc  tccggaacac agatttcaac tattgcagaa      60
agtgaagatt cacaggagtc agtggatagt gtaactgatt cccaaaagcg aagggaaatt    120
cttccaagga ggccttccta caggaaaatt ttgaatgact tatcttctga tgcaccagga    180
gtgccaagga ttgaagaaga gaagtctgaa gaggagactt cagcacctgc catcaccact    240
gtaacggtgc caactccaat ttaccaaact agcagtggac agtatattgc cattacccag    300
ggaggagcaa tacagctggc taacaatggt accgatgggg tacagggcct gcaaacatta    360
accatgacca atgcagcagc cactcagccg ggtactacca ttctacagta tgcacagacc    420
actgatggac agcagatctt agtgcccagc aaccaagttg ttgttcaagc tgcctctgga    480
gacgtacaaa cataccagat tcgcacagca cccactagca ctattgcccc tggagttgtt    540
atggcatcct ccccagcact tcctacacag cctgctgaag aagcagcacg aaagagagag    600
gtccgtctaa tgaagaacag ggaagcagct cgagagtgtc gtagaaagaa gaaagaatat    660
gtgaaatgtt tagaaaacag agtggcagtg cttgaaaatc aaaacaagac attgattgag    720
gagctaaaag cacttaagga cctttactgc cacaaatcag at                       762

<210> SEQ ID NO 6
<211> LENGTH: 254
<212> TYPE: PRT
<213> ORGANISM: Artificial Sequence
<220> FEATURE:
<223> OTHER INFORMATION: CREB DNA binding domain

<400> SEQUENCE: 6

Ser Ser Cys Lys Asp Leu Lys Arg Leu Phe Ser Gly Thr Gln Ile Ser
1               5                   10                  15

Thr Ile Ala Glu Ser Glu Asp Ser Gln Glu Ser Val Asp Ser Val Thr
            20                  25                  30
```

Asp Ser Gln Lys Arg Arg Glu Ile Leu Ser Arg Arg Pro Ser Tyr Arg
            35                  40                  45

Lys Ile Leu Asn Asp Leu Ser Ser Asp Ala Pro Gly Val Pro Arg Ile
 50                  55                  60

Glu Glu Glu Lys Ser Glu Glu Thr Ser Ala Pro Ala Ile Thr Thr
 65                  70                  75                  80

Val Thr Val Pro Thr Pro Ile Tyr Gln Thr Ser Ser Gly Gln Tyr Ile
                85                  90                  95

Ala Ile Thr Gln Gly Gly Ala Ile Gln Leu Ala Asn Asn Gly Thr Asp
            100                 105                 110

Gly Val Gln Gly Leu Gln Thr Leu Thr Met Thr Asn Ala Ala Ala Thr
            115                 120                 125

Gln Pro Gly Thr Thr Ile Leu Gln Tyr Ala Gln Thr Thr Asp Gly Gln
            130                 135                 140

Gln Ile Leu Val Pro Ser Asn Gln Val Val Gln Ala Ala Ser Gly
145                 150                 155                 160

Asp Val Gln Thr Tyr Gln Ile Arg Thr Ala Pro Thr Ser Thr Ile Ala
                165                 170                 175

Pro Gly Val Val Met Ala Ser Ser Pro Ala Leu Pro Thr Gln Pro Ala
            180                 185                 190

Glu Glu Ala Ala Arg Lys Arg Glu Val Arg Leu Met Lys Asn Arg Glu
            195                 200                 205

Ala Ala Arg Glu Cys Arg Arg Lys Lys Lys Glu Tyr Val Lys Cys Leu
            210                 215                 220

Glu Asn Arg Val Ala Val Leu Glu Asn Gln Asn Lys Thr Leu Ile Glu
225                 230                 235                 240

Glu Leu Lys Ala Leu Lys Asp Leu Tyr Cys His Lys Ser Asp
                245                 250

<210> SEQ ID NO 7
<211> LENGTH: 99
<212> TYPE: DNA
<213> ORGANISM: Artificial Sequence
<220> FEATURE:
<223> OTHER INFORMATION: nucleic acid sequence of VP16 activation domain

<400> SEQUENCE: 7
ctccacttag acggcgagga cgtggcgatg gcgcatgccg acgcgctaga cgatttcgat      60
ctggacatgt tggggacgg ggattccccg ggtccggga                              99

<210> SEQ ID NO 8
<211> LENGTH: 33
<212> TYPE: PRT
<213> ORGANISM: Artificial Sequence
<220> FEATURE:
<223> OTHER INFORMATION: VP16 activation domain

<400> SEQUENCE: 8

Leu His Leu Asp Gly Glu Asp Val Ala Met Ala His Ala Asp Ala Leu
1               5                   10                  15

Asp Asp Phe Asp Leu Asp Met Leu Gly Asp Gly Asp Ser Pro Gly Pro
            20                  25                  30

Gly

<210> SEQ ID NO 9
<211> LENGTH: 1026
<212> TYPE: DNA
<213> ORGANISM: Artificial Sequence
<220> FEATURE:
<223> OTHER INFORMATION: full-length amino acid sequence of CREB

<400> SEQUENCE: 9

```
atgaccatgg aatctggagc cgagaaccag cagagtggag atgcagctgt aacagaagct      60
gaaaaccaac aaatgacagt tcaagcccag ccacagattg ccacattagc ccaggtatct     120
atgccagcag ctcatgcaac atcatctgct cccaccgtaa ctctagtaca gctgcccaat     180
gggcagacag ttcaagtcca tggagtcatt caggcggccc agccatcagt tattcagtct     240
ccacaagtcc aaacagttca gtcttcctgt aaggacttaa aaagactttt ctccggaaca     300
cagatttcaa ctattgcaga aagtgaagat tcacaggagt cagtggatag tgtaactgat     360
tcccaaaagc gaagggaaat tctttcaagg aggccttcct acaggaaaat tttgaatgac     420
ttatcttctg atgcaccagg agtgccaagg attgaagaag agaagtctga agaggagact     480
tcagcacctg ccatcaccac tgtaacggtg ccaactccaa tttaccaaac tagcagtgga     540
cagtatattg ccattaccca gggaggagca atacagctgg ctaacaatgg taccgatggg     600
gtacagggcc tgcaaacatt aaccatgacc aatgcagcag ccactcagcc gggtactacc     660
attctacagt atgcacagac cactgatgga cagcagatct tagtgcccag caaccaagtt     720
gttgttcaag ctgcctctgg agacgtacaa acataccaga ttcgcacagc acccactagc     780
actattgccc ctggagttgt tatggcatcc tccccagcac ttcctacaca gcctgctgaa     840
gaagcagcac gaaagagaga ggtccgtcta atgaagaaca gggaagcagc tcgagagtgt     900
cgtagaaaga gaaagaataa tgtgaaatgt ttagaaaaca gagtggcagt gcttgaaaat     960
caaaacaaga cattgattga ggagctaaaa gcacttaagg acctttactg ccacaaatca    1020
gattaa                                                                1026
```

<210> SEQ ID NO 10
<211> LENGTH: 341
<212> TYPE: PRT
<213> ORGANISM: Artificial Sequence
<220> FEATURE:
<223> OTHER INFORMATION: amino acid sequence of the encoding region of CREB gene.

<400> SEQUENCE: 10

```
Met Thr Met Glu Ser Gly Ala Glu Asn Gln Gln Ser Gly Asp Ala Ala
1               5                   10                  15

Val Thr Glu Ala Glu Asn Gln Gln Met Thr Val Gln Ala Gln Pro Gln
            20                  25                  30

Ile Ala Thr Leu Ala Gln Val Ser Met Pro Ala Ala His Ala Thr Ser
        35                  40                  45

Ser Ala Pro Thr Val Thr Leu Val Gln Leu Pro Asn Gly Gln Thr Val
    50                  55                  60

Gln Val His Gly Val Ile Gln Ala Ala Gln Pro Ser Val Ile Gln Ser
65                  70                  75                  80

Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
        115                 120                 125

Ser Arg Arg Pro Ser Tyr Arg Lys Ile Leu Asn Asp Leu Ser Ser Asp
    130                 135                 140
```

```
Ala Pro Gly Val Pro Arg Ile Glu Glu Glu Lys Ser Glu Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
            180                 185                 190

Leu Ala Asn Asn Gly Thr Asp Gly Val Gln Gly Leu Gln Thr Leu Thr
        195                 200                 205

Met Thr Asn Ala Ala Ala Thr Gln Pro Gly Thr Thr Ile Leu Gln Tyr
    210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
                245                 250                 255

Ala Pro Thr Ser Thr Ile Ala Pro Gly Val Val Met Ala Ser Ser Pro
            260                 265                 270

Ala Leu Pro Thr Gln Pro Ala Glu Glu Ala Ala Arg Lys Arg Glu Val
        275                 280                 285

Arg Leu Met Lys Asn Arg Glu Ala Ala Arg Glu Cys Arg Arg Lys Lys
    290                 295                 300

Lys Glu Tyr Val Lys Cys Leu Glu Asn Arg Val Ala Val Leu Glu Asn
305                 310                 315                 320

Gln Asn Lys Thr Leu Ile Glu Glu Leu Lys Ala Leu Lys Asp Leu Tyr
                325                 330                 335

Cys His Lys Ser Asp
            340

<210> SEQ ID NO 11
<211> LENGTH: 1440
<212> TYPE: DNA
<213> ORGANISM: Artificial Sequence
<220> FEATURE:
<223> OTHER INFORMATION: DNA sequene for full-length amino acid sequence
      of VP16

<400> SEQUENCE: 11
atggacgcgg acggcgcttc gccaccaccc cccgcccgg  ccggggtcc caaaaacacc       60 ccggcggccc ctccgctgta cgcaacgggg cgcctgagcc aggcccagct catgccctcc     120
ccgcccatgc ccgtcccccc cgccgccctc tttaaccgtc tcctcgacga cttgggcttt     180
agcgcgggcc ccgcgctatg taccatgctc gatacctgga cgaggatttt gttttcggcg     240
ttaccgacca cgccgacct gtaccgggag tgtaaattcc tatcaacgct gcccagcgat      300
gtggtggaat gggggacgc gtacgtcccc gaacgcgccc aaatcgacat tcgcgcccac     360
ggcgacgtgg ccttcccgac gcttccggcc accgcgacg gcctcgggct ctactacgaa     420
gcgctctctc gtttcttcca cgccgagcta cggcgcgggg aggagagcta tcgaaccgtg     480
ttggccaact tctgctcggc cctgtaccgg tacctgcgcg ccagcgtccg gcagctgcac     540
cgccaggcgc acatgcgcgg acgcgatcgc gacctgggag aaatgctgcg cgccacgatc     600
gcggacaggt actaccgaga gaccgctcgt ctggcgcgtg ttctgttttt gcatttgtat     660
ctatttttga cccgcgagat cctatgggcc gcgtacgccg agcagatgat gcggcccgac     720
ctgtttgact gcctctgttg cgacctggag agctggcgtc agttggcggg tctgttccag     780
cccttcatgt tcgtcaacgg agcgctcacc gtcggggag tgccaatcga ggcccgccgg     840
ctgcgggagc taaaccacat tcgcgagcac cttaacctcc gctggtgcg cagcgcggct     900
```

-continued

```
acggaggagc caggggcgcc gttgacgacc cctcccaccc tgcatggcaa ccaggcccgc    960
gcctctgggt actttatggt gttgattcgg gcgaagttgg actcgtattc cagcttcacg   1020
acctcgccct ccgaggcggt catgcgggaa cacgcgtaca gccgcgcgcg tacgaaaaac   1080
aattacgggt ctaccatcga gggcctgctc gatctcccgg acgacgacgc ccccgaagag   1140
gcggggctgg cggctccgcg cctgtccttt ctccccgcgg acacacgcg cagactgtcg    1200 acggcccccc cgaccgatgt cagcctgggg acgagctcc acttagacgg cgaggacgtg    1260
gcgatggcgc atgccgacgc gctagacgat ttcgatctgg acatgttggg ggacggggat   1320
tccccgggtc cgggatttac ccccacgac tccgccccct acggcgctct ggatatggcc    1380
gacttcgagt ttgagcagat gtttaccgat gcccttggaa ttgacgagta cggtgggtag   1440
```

<210> SEQ ID NO 12
<211> LENGTH: 479
<212> TYPE: PRT
<213> ORGANISM: Artificial Sequence
<220> FEATURE:
<223> OTHER INFORMATION: amino acid sequence of the full-length encoding
      region of VP16 gene

<400> SEQUENCE: 12

```
Met Asp Ala Asp Gly Ala Ser Pro Pro Pro Arg Pro Ala Gly Gly
1               5                   10                  15

Pro Lys Asn Thr Pro Ala Ala Pro Pro Leu Tyr Ala Thr Gly Arg Leu
            20                  25                  30

Ser Gln Ala Gln Leu Met Pro Ser Pro Pro Met Pro Val Pro Pro Ala
        35                  40                  45

Ala Leu Phe Asn Arg Leu Leu Asp Asp Leu Gly Phe Ser Ala Gly Pro
    50                  55                  60

Ala Leu Cys Thr Met Leu Asp Thr Trp Asn Glu Asp Leu Phe Ser Ala
65                  70                  75                  80

Leu Pro Thr Asn Ala Asp Leu Tyr Arg Glu Cys Lys Phe Leu Ser Thr
                85                  90                  95

Leu Pro Ser Asp Val Val Glu Trp Gly Asp Ala Tyr Val Pro Glu Arg
            100                 105                 110

Ala Gln Ile Asp Ile Arg Ala His Gly Asp Val Ala Phe Pro Thr Leu
        115                 120                 125

Pro Ala Thr Arg Asp Gly Leu Gly Leu Tyr Tyr Glu Ala Leu Ser Arg
    130                 135                 140

Phe Phe His Ala Glu Leu Arg Ala Arg Glu Glu Ser Tyr Arg Thr Val
145                 150                 155                 160

Leu Ala Asn Phe Cys Ser Ala Leu Tyr Arg Tyr Leu Arg Ala Ser Val
                165                 170                 175

Arg Gln Leu His Arg Gln Ala His Met Arg Gly Arg Asp Arg Asp Leu
            180                 185                 190

Gly Glu Met Leu Arg Ala Thr Ile Ala Asp Arg Tyr Tyr Arg Glu Thr
        195                 200                 205

Ala Arg Leu Ala Arg Val Leu Phe Leu His Leu Tyr Leu Phe Leu Thr
    210                 215                 220

Arg Glu Ile Leu Trp Ala Ala Tyr Ala Glu Gln Met Met Arg Pro Asp
225                 230                 235                 240

Leu Phe Asp Cys Leu Cys Cys Asp Leu Glu Ser Trp Arg Gln Leu Ala
                245                 250                 255

Gly Leu Phe Gln Pro Phe Met Phe Val Asn Gly Ala Leu Thr Val Arg
```

-continued

```
                    260                 265                 270
Gly Val Pro Ile Glu Ala Arg Arg Leu Arg Glu Leu Asn His Ile Arg
        275                 280                 285

Glu His Leu Asn Leu Pro Leu Val Arg Ser Ala Ala Thr Glu Glu Pro
        290                 295                 300

Gly Ala Pro Leu Thr Thr Pro Pro Thr Leu His Gly Asn Gln Ala Arg
305             310                 315                 320

Ala Ser Gly Tyr Phe Met Val Leu Ile Arg Ala Lys Leu Asp Ser Tyr
                325                 330                 335

Ser Ser Phe Thr Thr Ser Pro Ser Glu Ala Val Met Arg Glu His Ala
            340                 345                 350

Tyr Ser Arg Ala Arg Thr Lys Asn Asn Tyr Gly Ser Thr Ile Glu Gly
        355                 360                 365

Leu Leu Asp Leu Pro Asp Asp Ala Pro Glu Glu Ala Gly Leu Ala
        370                 375                 380

Ala Pro Arg Leu Ser Phe Leu Pro Ala Gly His Thr Arg Arg Leu Ser
385             390                 395                 400

Thr Ala Pro Pro Thr Asp Val Ser Leu Gly Asp Glu Leu His Leu Asp
                405                 410                 415

Gly Glu Asp Val Ala Met Ala His Ala Asp Ala Leu Asp Asp Phe Asp
                420                 425                 430

Leu Asp Met Leu Gly Asp Gly Asp Ser Pro Gly Pro Gly Phe Thr Pro
        435                 440                 445

His Asp Ser Ala Pro Tyr Gly Ala Leu Asp Met Ala Asp Phe Glu Phe
        450                 455                 460

Glu Gln Met Phe Thr Asp Ala Leu Gly Ile Asp Glu Tyr Gly Gly
465                 470                 475
```

VP16-CREB FUSION GENE

BACKGROUND OF THE INVENTION

1. Field of the Invention

The present invention provides for a method of more stably and efficiently expressing transgenes in a cell. The present invention also provides a mammalian host cell that harbors VP16-CREB gene construct in its genome.

2. Description of the Background

Protein therapeutics has several advantages over conventional small molecule drugs. Because protein therapeutics generally works with improved specificity, they are less likely to interfere with normal biological processes and cause adverse effects. Proteins are also less prone to immune responses by human body than chemical drugs. These and other related benefits makes protein therapeutics to be one of the fastest growing segments in pharmaceutical industry.

Protein therapeutics, including antibody therapeutics, is produced using recombinant DNA technology in organisms such as bacteria, yeast, insect cells, and animal cells. For protein therapeutics, the gene coding for the protein is introduced into the host cells and the therapeutic proteins produced from the introduced gene are recovered from the host cells. By far, animal cells have been the most preferred host as they are capable of performing complex modifications to the proteins required for the desired function.

In most cases, protein therapeutics production from animal cells is carried out first by introducing the gene for therapeutics into the host cells. In most cases, a single cell that stably incorporates the gene into its own genome is selected and grown into a cell line for the production. Although several different types of animal cells have been used as host cells, Chinese Hamster Ovary (CHO) cells have been the most widely used.

Large scale production of protein therapeutics in animal cells, such as CHO cells, is technically demanding due to the low level of efficiency. In order to overcome this set back, people have used a derivative of CHO cells such as DG44 which is deficient in dihydrofolate reductase expression. In DG44 cell system, a genetic selection pressure is applied so that the stably incorporated transgenes can be amplified. The overall amount of therapeutic proteins produced from gene-amplified DG44 cells becomes increased simply because there are more copies of the gene available inside the cells.

However, the use of DG44 cells has a major drawback because of the lack of stability of amplified genes. Cell lines generated for recombinant therapeutics proteins using DG44 cells with gene amplification can show sudden decrease in the productivity during the large scale production process, due to the instability of the amplified genes. As the process of gene amplification itself is time consuming, this type of added delay can cause a significant delay in the overall processing time with a potential for a significant financial loss.

This clearly indicates that there is a need in the industry for an alternative and improved cell line to be used as a host for protein therapeutics production. In the present application, we report development of genetically engineered CHO cells that are capable of producing therapeutics protein at higher levels than the original CHO cells, and also show improved growth characteristics, making them suitable host for scale-up protein therapeutics manufacturing.

SUMMARY OF THE INVENTION

In one aspect, the invention is directed to a host mammalian cell comprising a nucleic acid encoding the VP16-CREB fusion protein integrated into its genome. The VP16-CREB fusion protein may include an activation domain of VP16 and DNA binding domain of CREB protein. In one aspect, the VP16-CREB fusion protein may include only essentially the activation domain of VP16 and DNA binding domain of CREB protein, and a linker that is covalently connects VP16 and CREB. The activation domain of VP16 may be as set forth in SEQ ID NO:8 or a fragment thereof so long as the fragment retains its activation activity. The DNA binding domain of CREB protein may be as set forth in SEQ ID NO:6, or a fragment thereof, so long as the fragment retains its DNA binding activity. In another aspect, the activation domain of VP16 may include amino acids sequence as set forth in SEQ ID NO:8 or a fragment thereof, and the DNA binding domain of CREB protein comprises amino acids sequence as set forth in SEQ ID NO:6 or a fragment thereof. The amino acid sequence may be as encoded by nucleic acid having SEQ ID NO:1. In the host mammalian cell as described above, VP16-CREB fusion protein may be expressed stably. The host mammalian cell may be a CHO cell.

In another aspect, the host mammalian cell may further include a second transgene nucleic acid that has a promoter containing one or more CREB binding sites. The promoter may be CMV promoter, which includes cytomegalovirus immediate early enhancer promoter.

In yet another aspect, the invention is directed to a method of producing a protein encoded by an exogenous transgene in a host mammalian cell, including transfecting the mammalian host cell as described above with an expression vector comprising a second transgene, expressing the protein encoded by the exogenous second transgene nucleic acid in the mammalian host cell to produce the protein. The second transgene may be an antibody or a component of an antibody.

In another aspect, the invention is directed to a method of growing mammalian cell more efficiently and at higher density compared with unmodified cells, including growing the mammalian cells as described above. The mammalian cell may be a CHO cell.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE INVENTION

Figure 1:
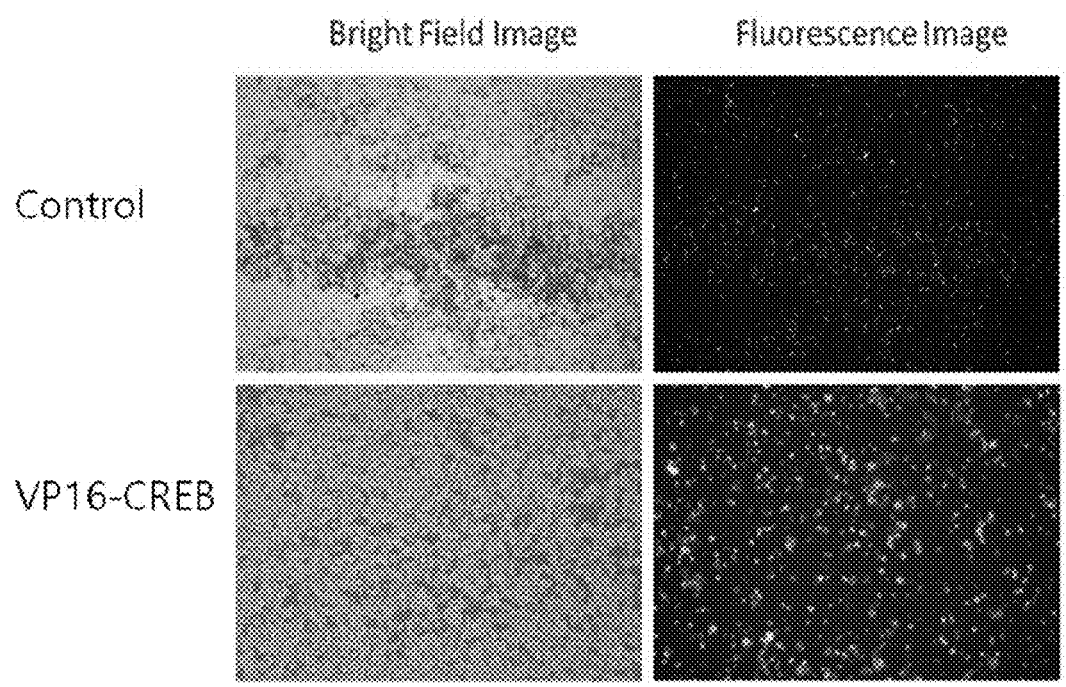
FIG. 1. Effect of transiently over-expressing VP16-CREB on hrGFP expression from stable pool cells (CHO-k1-LG). A stable pool of CHO-k1 cells (CHO-k1-LG) was prepared by transfecting CHO-k1 cells using a plasmid vector containing both the hrGFP gene and the firefly luciferase gene under the control of CMV promoter and selecting them using an appropriate antibiotic. CHO-k1-LG cells were then transiently transfected with a plasmid vector containing VP16-CREB gene or an empty vector as a control and were observed using a fluorescence microscope for the level of GFP expression 22 hours after transfection.

In the present application, "a" and "an" are used to refer to both single and a plurality of objects.

As described in greater detail below, applicants have discovered a method of using a mammalian host cell harboring VP16-CREB fusion gene construct, to enhance the biological activity of the host cell in producing transgene product effectively and stably, and in which the growth of the cells occurs without aggregation.

As used herein, "fusion construct" or "fusion product", refers to the combination of two genes or fragments of genes joined by a linker, which nucleic acid construct is expressed to the fusion protein. The resultant fusion product is capable of being biologically active in binding to other proteins or nucleic acids.

As used herein, "fragments" or "functional derivatives" refers to biologically active amino acid sequence variants and fragments of the native protein of the present invention, as well as covalent modifications, including derivatives obtained by reaction with organic derivatizing agents, post-translational modifications, derivatives with nonproteinaceous polymers, and immunoadhesins.

As used herein, "DNA binding domain" refers to the portion of a protein that binds to the nucleic acid and includes the minimal portion of the receptor that is necessary to bind the nucleic acid.

As used herein, "linked" refers to direct or indirect connection between the two proteins or fragments of proteins to create a fusion product. Both a direct fusion between these two domains or indirect fusion as by the domains being separated by a linker or an intervening domain or element are contemplated, so long as the activity of the fusion product is present.

As used herein, "second transgene" refers to an exogenous gene that is transfected into a host cell in which VP16-CREB fusion protein is expressed. "Second transgene" herein is meant to merely distinguish itself from a "first transgene", which could be considered to be the exogenous VP16-CREB fusion polypeptide encoding gene that is integrated into a mammalian host cell. Thus, by "second transgene", the host cell may contain multiple second transgenes without being limited in number to any one particular type of gene. In other words, transgene A and transgene B could both be considered to be "second transgene" and could co-exist and be co-expressed in a host cell, and both transgenes may be referred to as a "second transgene".

VP16

VP16 is also known as Vmw65 or α-TIF (Trans Inducing Factor) is a trans-acting protein that forms a complex with the host transcription factors Oct-1 and HCF to induce immediate early gene transcription in the herpes simplex viruses.

CREB

CREB (cAMP response element-binding protein) is a cellular transcription factor. It binds to certain DNA sequences called cAMP response elements (CRE), thereby increasing or decreasing the transcription of the downstream genes. CREB is closely related in structure and function to CREM (cAMP response element modulator) and ATF-1 (activating transcription factor-1) proteins. CREB proteins are expressed in many animals, including humans.

VP16-CREB

Proteins are produced from a gene coding for the protein. Genes contain information needed to make functional proteins. The process is complex and tightly controlled within a cell. It consists of two major steps: transcription and translation. During the process of transcription, the information stored in a gene's DNA is transferred to RNA in the cell nucleus. The information in RNA is then used to put together amino acids in a sequential order to assemble a protein which then forms into its functional state.

Gene transcription is achieved in multiple steps and starts with the regulation of transcription initiation. Most eukaryotes possess methods of regulating transcription initiation on a gene-by-gene basis. The transcription of a gene can be regulated by cis-acting elements within the regulatory regions of the DNA called promoters and enhancers, and trans-acting factors that include transcription factors, co-factors and the basal transcription complex.

In the current invention, CHO cell is genetically modified by stably transfecting with the VP16-CREB gene, so that the cell can become more efficient in transcribing exogenously introduced genes. The VP16-CREB gene contains sequences for the activation domain of a viral protein VP16 fused to the DNA binding domain of human CREB protein. While wild type CREB requires signal-dependent activation for its function as a transcription factor, VP16-CREB is constitutively active. Although it is plausible to expect that over-expression of VP16-CREB in CHO cells will help increase transgene expression from a CRE containing promoter, an additional step has to be taken to overcome a potential apoptotic effect of over-expressing a constitutively active form of CREB. It has been reported by Saeki et al (1999) that over-expression of CREB causes apoptotic cell death in CHO cells. During the stable clone generation over-expressing VP16-CREB gene, cells were selected based on their ability to overcome not only antibiotics selection pressure but also a potential apoptic effect of VP16-CREB. The resulting genetically modified CHO clones show improved efficiency in transgene expression and also show improved growth characteristics as an added benefit for them to be used as the host for protein therapeutics manufacturing purpose.

Transcription factors (sometimes called sequence-specific DNA-binding factors) are proteins that bind to specific DNA sequences, thereby controlling transcription of genetic information from DNA to mRNA. Transcription factors perform this function alone or with other proteins in a complex, by promoting (as an activator), or blocking (as a repressor) the recruitment of RNA polymerase to specific genes.

A defining feature of transcription factors is that they contain one or more DNA-binding domains (DBDs), which attach to specific sequences of DNA adjacent to the genes that they regulate. Transcription factors also contain activation domain separate from the DNA-binding domain.

Gene promoters contain specific DNA sequences and response elements that provide a secure initial binding site for RNA polymerase and for transcription factors that recruit RNA polymerase. Transcription of a gene is thus regulated by transcription factors available inside the cells that are capable of binding to the promoter region of the particular gene of interest. In other words, the interaction between the promoter region of a gene with various transcription factors can determine the amount of proteins produced from that particular gene.

In terms of the gene promoter used for the control of therapeutics genes, cytomegalovirus immediate early enhancer promoter (collectively termed as CMV promoter) is one of the most widely used promoters. The reason for this is because it works with high efficiency in many mammalian cell types including CHO cells. CMV promoter spans 400-700 base pairs and contains putative binding sites for various transcription factors, including cAMP-responsive element binding protein (CREB). CREB is a transcription factor involved in the expression of a number of cellular genes. CMV promoter contains various sites that matches or homologous with CREB DNA-binding consensus sequence. It is generally believed that CREB interacts with these sites to activate gene expression from CMV promoter.

CREB belongs to bZIP superfamily transcript factors and contains a C-terminal basic domain that mediates DNA binding and a leucine zipper domain that facilitates dimerization. CREB binds to the cAMP response element (CRE) which consists of a palindromic consensus sequence TGACGTCA. While the bZIP domain mediates DNA binding and dimerization, the remaining domains of CREB family member serve to facilitate interactions with coactivators and components of the transcriptional machinery that ultimately carry out RNA synthesis.

CREB isoforms contains the bZIP domain and two glutamine rich domains, referred to as Q1 and Q2 that are separated by the kinase inducible domain (KID). A serine residue within the KID domain (Ser-133) is known to be phosphorylated for the activation of the transcription factor in response to various intracellular signals. The activation process also involves binding of the transcriptional coactivator, CREB binding protein (CBP) to CREB through the KID domain. Q2/CAD domain is known to interact with components of the basal transcriptional machinery.

CREB is involved in various cellular signaling processes related to cell growth and development and nervous system functions. While it is still not completely understood how CREB facilitates various cellular processes in a delicate and co-ordinated fashion, it is believed that the availability of CREB proteins within the cell can be limiting under certain circumstances. Especially, when a foreign gene under the control of CRE-containing promoter is introduced into the cells, it is likely that the introduced gene will compete for CREB with endogenous genes. Cell lines generated for the purpose of protein therapeutics production contain multiple copies of the therapeutic protein gene incorporated inside the host cell genome. If CMV promoter is used for the expression of the therapeutics gene, then CMV promoter will compete for CREB with endogenous genes, as CMV promoter has a number of binding sites for CREB. If the available amount of CREB is limiting inside the cells, expression of the therapeutics gene from the CMV promoter will be set to the level lower than maximum possible levels.

In order to overcome this potential limitation by the availability of CREB proteins inside the host cells, we have generated CHO cells capable of stably expressing a constitutively active form of CREB. CREB is known to be activated by phosphorylation on Ser-133 residue in response to several different cellular signaling pathways. This phosphorylation-dependent activation of CREB is required for the protein to act as a transcription activator. Therefore, a constitutively active CREB is used so that the resulting transcription factor can directly work on CMV promoter without the need for signal-dependent activation process. Constitutively active CREB is a fusion between the activation domain of herpes simplex virus VP16 protein and the DNA binding domain of CREB. It is expressed from a fusion gene containing SV40 large T nuclear localization sequence (24 nucleotides), an activation domain of VP16 (amino acids 413-445, 99 nucleotides), a linker (48 bp), a DNA binding domain from human CREB gene (amino acids 88-341, 762 nucleotides) and other sequences.

SEQ ID NO:1 describes VP16-CREB entire sequence.

(SEQ ID NO: 1)
atgaagctactgtcttctatcgaacaagcatgcccaaaaaagaagagaaa ggtagatgaatttcctgggatctctactgctcctccaaccgatgtcagcc tgggcgacgaactccacttagacggcgaggacgtggcgatggcgcatgcc gacgcgctagacgatttcgatctggacatgttgggggacggggattcccc gggtccgggatctccagcgattccgtcgacaccacctactccctctccag cgatcgcctcttcctgtaaggacttaaaaagacttttctccggaacacag atttcaactattgcagaaagtgaagattcacaggagtcagtggatagtgt aactgattcccaaaagcgaagggaaattctttcaaggaggccttcctaca ggaaaattttgaatgacttatcttctgatgcaccaggagtgccaaggatt gaagaagagaagtctgaagaggagacttcagcacctgccatcaccactgt aacggtgccaactccaatttaccaaactagcagtggacagtatattgcca ttacccaggaggagcaatacagctggctaacaatggtaccgatgggta cagggcctgcaaacattaaccatgaccaatgcagcagccactcagccggg tactaccattctacagtatgcacagaccactgatggacagcagatcttag tgcccagcaaccaagttgttgttcaagctgcctctggagacgtacaaaca taccagattcgcacagcacccactagcactattgcccctggagttgttat ggcatcctccccagcacttcctacacagcctgctgaagaagcagcacgaa agagagaggtccgtctaatgaagaacagggaagcagctcgagagtgtcgt agaaagaagaaagaatatgtgaaatgtttagaaaacagagtggcagtgct tgaaaatcaaaacaagacattgattgaggagctaaaagcacttaaggacc tttactgccacaaatcagatgtttaa SEQ ID NO:2 describes a fusion sequence comprising 33 nucleotides sequence from GAL4, SV40 large T nuclear targeting sequence, and herpes simplex virus VP16 transactivation domain sequence.

(SEQ ID NO: 2)
atgaagctactgtcttctatcgaacaagcatgcccaaaaaagaagagaaa ggtagatgaatttcctgggatctctactgctcctccaaccgatgtcagcc tgggcgacgaactccacttagacggcgaggacgtggcgatggcgcatgcc gacgcgctagacgatttcgatctggacatgttgggggacggggattcccc gggtccggga SEQ ID NO:3 describes IgA linker encoding the polypeptide SPAIPSTPPTPSP (SEQ ID NO:4).

(SEQ ID NO: 3)
tctccagcgattccgtcgacaccacctactccctctcca

SEQ ID NO:5 describes DNA encoding CREB DNA binding domain sequence.

(SEQ ID NO: 5)
tcttcctgtaaggacttaaaaagacttttctccggaacacagatttcaac tattgcagaaagtgaagattcacaggagtcagtggatagtgtaactgatt cccaaaagcgaagggaaattctttcaaggaggccttcctacaggaaaatt ttgaatgacttatcttctgatgcaccaggagtgccaaggattgaagaaga gaagtctgaagaggagacttcagcacctgccatcaccactgtaacggtgc caactccaatttaccaaactagcagtggacagtatattgccattacccag ggaggagcaatacagctggctaacaatggtaccgatggggtacagggcct gcaaacattaaccatgaccaatgcagcagccactcagccgggtactacca ttctacagtatgcacagaccactgatggacagcagatcttagtgcccagc aaccaagttgttgttcaagctgcctctggagacgtacaaacataccagat tcgcacagcacccactagcactattgcccctggagttgttatggcatcct ccccagcacttcctacacagcctgctgaagaagcagcacgaaagagagag gtccgtctaatgaagaacagggaagcagctcgagagtgtcgtagaaagaa gaaagaatatgtgaaatgtttagaaaacagagtggcagtgcttgaaaatc aaaacaagacattgattgaggagctaaaagcacttaaggacctttactgc cacaaatcagat SEQ ID NO:6 describes amino acid sequence of CREB DNA binding domain sequence.

(SEQ ID NO: 6)
SSCKDLKRLFSGTQISTIAESEDSQESVDSVTDSQKRREILSRRPSYRKI

LNDLSSDAPGVPRIEEEKSEEETSAPAITTVTVPTPIYQTSSGQYIAITQ

GGAIQLANNGTDGVQGLQTLTMTNAAATQPGTTILQYAQTTDGQQILVPS

NQVVVQAASGDVQTYQIRTAPTSTIAPGVVMASSPALPTQPAEEEAARKRE

VRLMKNREAARECRRKKKEYVKCLENRVAVLENQNKTLIEELKALKDLYC

HKSD

SEQ ID NO:7 describes nucleic acid sequence of VP16 activation domain.

(SEQ ID NO: 7)
ctccacttagacggcgaggacgtggcgatggcgcatgccgacgcgctagac gatttcgatctggacatgttgggggacggggattccccgggtccggga SEQ ID NO:8 describes amino acid sequence of VP16 activation domain (SEQ ID NO:8)
LHLDGEDVAMAHADALDDFDLDMLGDGDSPGPG SEQ ID NO:9 describes DNA sequence for full-length amino acid sequence of CREB.

(SEQ ID NO: 9)
atgaccatggaatctggagccgagaaccagcagagtggagatgcagctgta acagaagctgaaaaccaacaaatgacagttcaagcccagccacagattgcc acattagcccaggtatctatgccagcagctcatgcaacatcatctgctccc accgtaactctagtacagctgcccaatgggcagacagttcaagtccatgga gtcattcaggcggcccagccatcagttattcagtctccacaagtccaaaca gttcagtcttcctgtaaggacttaaaaagacttttctccggaacacagatt -continued
tcaactattgcagaaagtgaagattcacaggagtcagtggatagtgtaact gattcccaaaagcgaagggaaattctttcaaggaggccttcctacaggaaa attttgaatgacttatcttctgatgcaccaggagtgccaaggattgaagaa gagaagtctgaagaggagacttcagcacctgccatcaccactgtaacggtg ccaactccaatttaccaaactagcagtggacagtatattgccattacccag ggaggagcaatacagctggctaacaatggtaccgatggggtacagggcctg caaacattaaccatgaccaatgcagcagccactcagccgggtactaccatt ctacagtatgcacagaccactgatggacagcagatcttagtgcccagcaac caagttgttgttcaagctgcctctggagacgtacaaacataccagattcgc acagcacccactagcactattgccctggagttgttatggcatcctcccca gcacttcctacacagcctgctgaagaagcagcacgaaagagagaggtccgt ctaatgaagaacagggaagcagctcgagagtgtcgtagaaagaagaaagaa tatgtgaaatgtttagaaaacagagtggcagtgcttgaaaatcaaaacaag acattgattgaggagctaaaagcacttaaggacctttactgccacaaatca gattaa SEQ ID NO:10 describes amino acid sequence of the encoding region of CREB gene.

(SEQ ID NO: 10)
MTMESGAENQQSGDAAVTEAENQQMTVQAQPQIATLAQVSMPAAHATSSA

PTVTLVQLPNGQTVQVHGVIQAAQPSVIQSPQVQTVQSSCKDLKRLFSGT

QISTIAESEDSQESVDSVTDSQKRREILSRRPSYRKILNDLSSDAPGVPR

IEEEKSEEETSAPAITTVTVPTPIYQTSSGQYIAITQGGAIQLANNGTDG

VQGLQTLTMTNAAATQPGTTILQYAQTTDGQQILVPSNQVVVQAASGDVQ

TYQIRTAPTSTIAPGVVMASSPALPTQPAEEAARKREVRLMKNREAAREC

RRKKKEYVKCLENRVAVLENQNKTLIEELKALKDLYCHKSD*

SEQ ID NO:11 describes DNA sequence for full-length amino acid sequence of VP16.

(SEQ ID NO: 11)
atggacgcggacggcgcttcgccaccacccccgcccggccgggggtccc aaaaacaccccggcggcccctccgctgtacgcaacggggcgcctgagccag gcccagctcatgccctcccgcccatgcccgtcccccccgccgccctcttt aaccgtctcctcgacgacttgggctttagcgcggggccccgcgctatgtacc atgctcgatacctggaacgaggatttgttttcggcgttaccgaccaacgcc gacctgtaccgggagtgtaaattcctatcaacgctgcccagcgatgtggtg gaatgggggacgcgtacgtccccgaacgcgcccaaatcgacattcgcgcc cacggcgacgtggccttcccgacgcttccggccaccgcgacggcctcggg ctctactacgaagcgctctctcgtttcttccacgccgagctacgggcgcgg gaggagagctatcgaaccgtgttggccaacttctgctcggccctgtaccgg tacctgcgcgccagcgtccggcagctgcaccgccaggcgcacatgcgcgga cgcgatcgcgacctgggagaaatgctgcgcgccacgatcgcggacaggtac taccgagagaccgctcgtctggcgcgtgttctgttttgcatttgtatcta ttttttgacccgcgagatcctatgggccgcgtacgccgagcagatgatgcgg cccgacctgtttgactgcctctgttgcgacctggagagctggcgtcagttg gcgggtctgttccagcccttcatgttcgtcaacggagcgctcaccgtccgg ggagtgccaatcgaggcccgccggctgcgggagctaaaccacattcgcgag caccttaacctcccgctggtgcgcagcgcggctacggaggagccaggggcg ccgttgacgacccctcccaccctgcatggcaaccaggcccgcgcctctggg tactttatggtgttgattcgggcgaagttggactcgtattccagcttcacg acctcgccctccgaggcggtcatgcgggaacacgcgtacagccgcgcgcgt acgaaaaacaattacgggtctaccatcgagggcctgctcgatctcccggac gacgacgccccgaagaggcggggctggcggctccgcgcctgtcctttctc cccgcgggacacacgcgcagactgtcgacggccccccgaccgatgtcagc ctggggacgagctccacttagacggcgaggacgtggcgatggcgcatgcc gacgcgctagacgatttcgatctggacatgttgggggacggggattcccg ggtccgggatttaccccccacgactccgcccctacggcgctctggatatg gccgacttcgagtttgagcagatgtttaccgatgcccttggaattgacgag tacggtgggtag SEQ ID NO:12 describes amino acid sequence of the full-length encoding region of VP16 gene.

(SEQ ID NO: 12)
MDADGASPPPPRPAGGPKNTPAAPPLYATGRLSQAQLMPSPPMPVPPAALF

NRLLDDLGFSAGPALCTMLDTWNEDLFSALPTNADLYRECKFLSTLPSDVV

EWGDAYVPERAQIDIRAHGDVAFPTLPATRDGLGLYYEALSRFFHAELRAR

EESYRTVLANFCSALYRYLRASVRQLHRQAHMRGRDRDLGEMLRATIADRY

YRETARLARVLFLHLYLFLTREILWAAYAEQMMRPDLFDCLCCDLESWRQL

AGLFQPFMFVNGALTVRGVPIEARRLRELNHIREHLNLPLVRSAATEEPGA

PLTTPPTLHGNQARASGYFMVLIRAKLDSYSSFTTSPSEAVMREHAYSRAR

TKNNYGSTIEGLLDLPDDDAPEEAGLAAPRLSFLPAGHTRRLSTAPPTDVS

LGDELHLDGEDVAMAHADALDDFDLDMLGDGDSPGPGFTPHDSAPYGALDM

ADFEFEQMFTDALGIDEYGG*

Nucleic Acid

The present invention provides for a nucleic acid encoding a fusion polypeptide wherein the fusion polypeptide comprises a first subunit comprising at least one copy of the activation domain of viral VP16, and a second subunit comprising at least one copy of the DNA binding domain of CREB, which is stably integrated into the genome of a host mammalian cell.

Also provided is an expression vector comprising a nucleic acid molecule encoding the VP16-CREB fusion construct, and also in particular encoding a second transgene product, of the invention as described herein, wherein the nucleic acid molecule is operatively linked to an expression control sequence. Also provided is a host-vector system for the production of a fusion polypeptide or the second transgene product, which comprises the expression vector of the invention which has been introduced into a host cell suitable for expression of the fusion polypeptide. The suitable host cell may be a bacterial cell such as E. coli, a yeast cell, such as *Pichia pastoris*, an insect cell, such as *Spodoptera frugiperda*, or a mammalian cell, such as a COS or CHO cell. Preferred is a mammalian cell in which the VP16-CREB fusion gene construct is integrated into the genome of the host cell, into which the second transgene containing vector is introduced, which causes the second transgene product to be optimally expressed. Preferably, the mammalian cell is CHO.

The present invention also provides for methods of producing the second transgene product by growing cells of the host-vector system described herein, under conditions permitting production of the second transgene product and recovering the second transgene product so produced. The second transgene products useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The second transgene product may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, the fusion protein or second transgene product includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the second transgene product of the invention are genetically engineered to produce them by, for example, transfection, transduction, electropration, or microinjection techniques.

In addition, the present invention contemplates use of the second transgene product described herein in tagged form.

Any of the methods known to one skilled in the art for the insertion of DNA fragments into a vector may be used to construct expression vectors encoding the second transgene product of the invention using appropriate transcriptional/translational control signals and protein coding sequences. These methods may include in vitro recombinant DNA and synthetic techniques and in vivo recombinations (genetic recombination). Expression of nucleic acid sequence encoding the second transgene product of the invention may be regulated by a second nucleic acid sequence so that the second transgene product is expressed in a host transformed with the recombinant DNA molecule. For example, expression of the second transgene product described herein may be controlled by any promoter/enhancer element known in the art. Promoters which may be used to control expression of the second transgene product include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3'long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a second transgene product as described herein, are used to transfect the host and thereby direct expression of such nucleic acid to produce second transgene product which may then be recovered in biologically active form.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The second transgene product, of the present invention, may be expressed in the host cells transiently, constitutively or permanently.

The fusion gene construct, preferably VP16-CREB, may be inserted into the genome of its host cell, which helps the host cell to express a second transgene that is transfected into the cell, in which case all of the protein expression and purification methods described above may be applied to the expression and purification of the second transgene.

The V23 cell line of the present invention was named as CHO-ks1 and deposited at the Korean Collection for Type Cultures (KCTC) of the Korea Research Institute of Bioscience and Biotechnology (KRIBB), 125 Gwahak-ro, Yuseong-gu, Daejeon 305-806, Republic of Korea, on May 11, 2015 (Accession No: KCTC12810BP).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Materials

CHO Cells:
CHO cells were purchased from ATCC (Manassas, Va.)
Item Number: CCL-61
Description: CHO-k1; Ovary, Chinese Hamster (*Cricetulus griseus*)
Geneticin: Life Technologies (Item #10131)
CDM4CHO medium: Thermo Scientific (Hyclone, SH30557)
L-Glutamine: Lonza (17-605E)
DPBS: Lonza (17-512F/12)
F-12K medium: ATCC (30-2004)
Fetal Bovine Serum: Invitrogen (10438026)
Trypsin 0.25% EDTA: Invitrogen (25200072)

Example 2

A plasmid vector containing the VP16-CREB fusion gene under the control of CMV promoter and the neomycin-resistance gene as a selectable marker was prepared, using Promega's pFN10A (ACT) Flexi Vector. The resulting plasmid was named pVP16-CREB.

The effect of overexpressing VP16-CREB fusion gene in CHO cells on the expression of stably transfected gene under CMV promoter control was tested first under conditions similar to therapeutics gene expression cases. For this, we have generated a stable CHO-k1 cell line expressing both firefly luciferase gene and human recombinant green fluorescence gene (hrGFP) under the control of CMV promoter separately. This was done by transfecting CHO-k1 cells with a plasmid vector containing the two genes and neomycin-resistance gene as a selectable marker. This vector is named as pCN-LG. A pool of stably expressing cells was prepared by adding G-418 in the culture medium and growing cells for 2-3 weeks. Stable pool of CHO-k1 cells (CHO-k1-LG) expressing these double reporter genes were then made into liquid nitrogen stocks for subsequent uses.

In order to test the effect of overexpressing VP16-CREB fusion gene on stably transfected gene expression, CHO-k1-LG cells grown in suspension culture were transiently tranfected with pVP16-CREB plasmid vector. For the experiment, 1.5 million CHO-k1-LG cells were transfected with 1 μg of the pVP16-CREB plasmid DNA plus 2 μg of control vector which does not contain either luciferase gene or hrGFP gene. Another batch of cells was transfected with 3 μg of the control vector only for comparison. The experiment was done in duplicates. Transfected cells were maintained in 12 well plates. Approximately 22 hours after the transfection, cells were observed under a fluorescence microscope for the expression of hrGPF from transfected cells. The results show a much higher hrGFP expression level from cells transfected with pVP16-CREB containing vector compared to cells transfected with a control plasmid.

The cells used for the observation under the fluorescence microscope were further incubated for an additional 24 hours and then harvested for luciferase assay. Cells were detached from the plates and first counted for the cell number and viability. Cells were then harvested and resuspended in DPBS and assayed for luciferase activity using Pormega's Blight Glow Luciferase assay kit.

The result in FIG. 1 shows that transiently overexpressing VP16-CREB causes approximately 11 fold increase (1.37 for control vs 15.01 for VP16-CREB) in the expression of luciferase gene from stably expressing cell pool (CHO-k1-LG).

Figure 2:
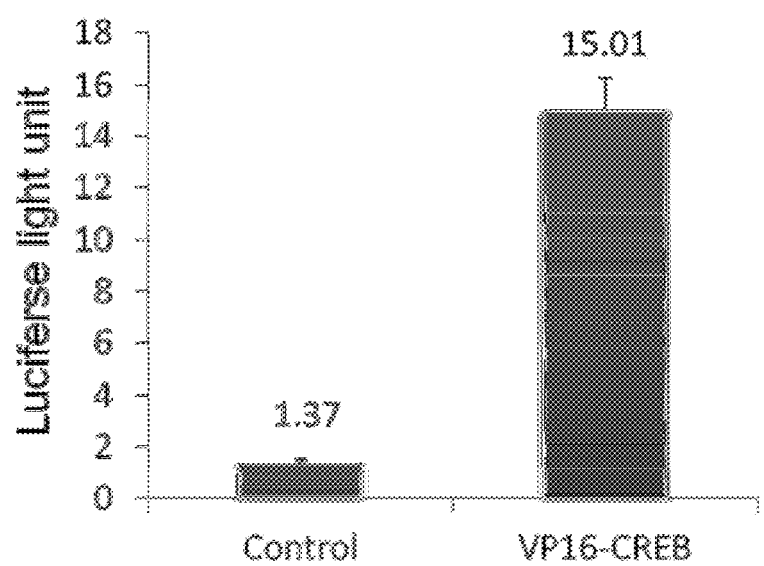
FIG. 2. Effect of transiently over-expressing VP16-CREB on luciferase gene expression from stable pool cells (CHO-k1-LG). Cells used for the observation in FIG. 1 were further incubated for an additional 24 hours and harvested for cell count and viability tests, and then for luciferase assay. Luciferase assay was performed in duplicates.

Interestingly, cells transfected with the VP16-CREB plasmid showed increased post-transfection viability compared to cells transfected with the control plasmid (51.1% vs 26.2%). This indicates that overexpression of VP16-CREB may also help increasing the rate of survival of cells under suboptimum conditions. See FIG. 2 and below.

|  | | Cell Count ($10^5$ cells/ml) | Viability (%) |
|---|---|---|---|
| VP16-CREB | Duplicate#1 | 2.85 | 45.1 |
|  | Duplicate#2 | 5.14 | 57.1 (average 51.1%) |
| Control | Duplicate#1 | 1.23 | 22.7 |
|  | Duplicate#2 | 2.21 | 29.7 (average 26.2%) |

This result is quite contrary to a report published by Saeki et al in 1999 in Biochemical Journal, in which the authors observed induction of apoptosis by aberrant expression of CREB in several different cell types including CHO. This indicates that depending on circumstances CREB over-expression may be used as a positive factor for the selection of VP16-CREB stable cell line.

Example 3

Based on these results, an experiment was performed to generate CHO-k1 cell line stably expressing VP16-CREB. CHO-k1 cells preadapted to suspension culture in chemically defined medium were used for the experiment. Two million cells were used for transfection by electroporation using 2.5 μg of plasmid DNA. Transfection was performed five times for total 10 million cells and cells were pooled together in a 50 ml bioreactor with 10 ml of culture medium (CDM4CHO). Two days after transfection, G-418 was added to the medium at 400 μg/ml concentration for the selection of stably transfected cells. Cell medium (with G-418) was replaced every 3-5 days, and cell counting and viability check were performed every 24 hours. Approximately 17 days after the transfection, stably transfected cells surviving G-418 selection were plated in six 96-well plates by limiting dilution at 1 cell per well density in 200 μl of 1:1 mixture CDM4CHO and a conditioned medium prepared from CHO-k1 cells, plus 400 μg/ml G-418. Cells were continuously observed under the microscope and wells with a clearly defined single colony were marked. On day 18 after the plating, 24 colonies were selected and expanded into a 24 well plate, in 1 ml of CDM4CHO with G-418.

As over-expression of CREB is known to cause apoptotic cell death in CHO cells (Saeki et al, 1999), these 24 surviving clones were the ones overcoming not only G-418 selection pressure but also a potential apoptotic effect of the constitutively active form of CREB. These cells were further expanded into 6 well plates and then into 50 ml bioreactors. Cell growth was monitored every 1-2 days. After approximately 2 weeks of expansion and growth, cells were narrowed down to 8 clones based on their growth characteristics, especially overcoming potential apoptotic effect of CREB over-expression The incorporation of the VP16-CREB gene was verified by PCR amplification of the genomic DNA isolated from the 8 selected clones. Genomic DNA was isolated using 1 million cells and using Qiagen's QiaAmp mini-DNA kit. 200 ng of the purified DNA was used in PCR reaction, using a primer set binding internally within the VP16-CREB gene sequence which will produce an amplicon at approximately 380 bp. The amplicons were resolved in 1.5% agarose DNA gel.

Figure 3:
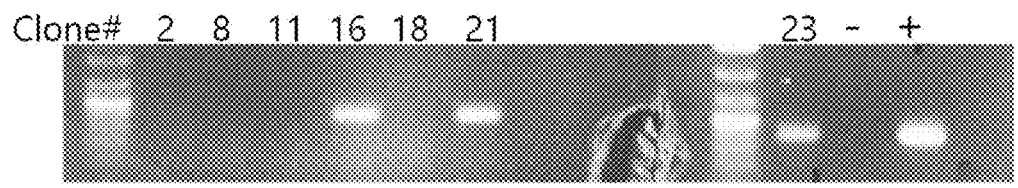
FIG. 3. Verification of stable incorporation of VP16-CREB fusion gene in stably transfected CHO-k1 cell genome. A set of PCR primers was used to amplify approximately 380 bp region within the fusion gene using genomic DNA samples isolated from cell lines stably transfected with VP16-CREB fusion gene as the template. Amplicons from 7 different clones were resolved using a 1.5% agarose gel.

The result in FIG. 3 shows that among the 8 clones only 3 clones (#16, #21, and #23) have VP16-CREB gene incorporated inside their genome, producing 380 bp amplicon. So, these 3 clones were further tested for their capability.

Example 4

In order to further verify the actual expression of VP16-CREB gene inside the cells of the selected clones, quantitative PCR reaction was performed using RNA isolated from clones#16, 21, and 23. Two million cells were used for total RNA isolation using Qiagen RNeasy mini kit. One μg of RNA was then converted into cDNA using Invitrogen's VILO cDNA synthesis kit. Finally Q-PCR reaction was performed using GAPDH as an internal control, and using 100 ng of each cDNA and SYBR master mix. cDNA prepared from CHO-k1 cells, clone #7, #8 and stable pool cells were also used in the reaction.

Figure 4:
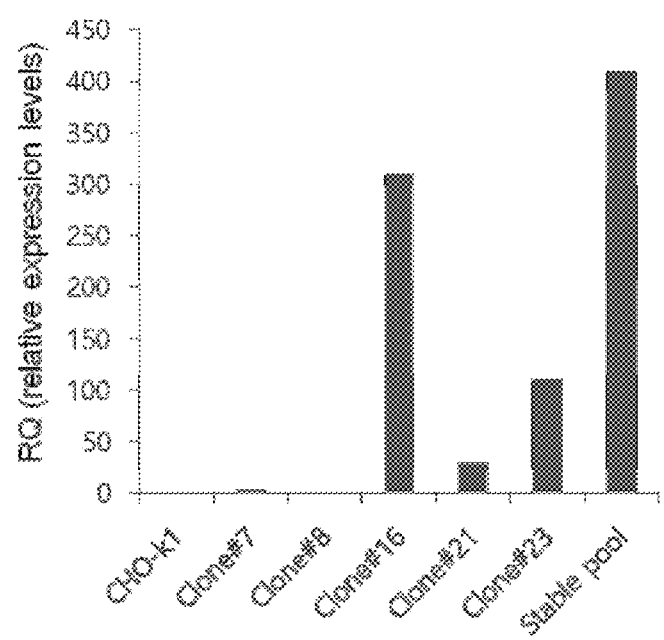
FIG. 4. Detection of relative expression levels of the VP16-CREB fusion gene from stable cell lines using QPCR. One μg of RNA isolated from CHO-k1, clones 7, 8, 16, 21, 23 and stable pool cells, respectively, was converted into cDNA. Q-PCR reaction was performed using GAPDH as an internal control, and using 100 ng of each cDNA and SYBR master mix.

The result in FIG. 4 clearly shows that while CHO-k1, clone #7 and #8 do not show expression of VP16-CREB, clone #16, #21, #23 and stable pool cells show substantial levels of expression. This result matches with genomic PCR verification result shown in FIG. 3. From these results, clone #16 and #23 were chosen for final testing.

Example 5

As clones #16 and #23 expressed substantial levels of VP16-CREB stably, the ability of these cells to increase CMV promoter driven expression of transgenes were tested by transiently transfecting a plasmid vector expressing both luciferase gene and hrGFP gene under the control of CMV promoter (plasmid pCN-LG). For the transfection, 3 million cells were used with 5 μg of pCN-LG DNA. Cells were plated out and maintained in a 6 well plate. CHO-k1 cells were also included as a control. Two days after the transfection, cells were harvested and luciferase assay was performed as before.

Figure 5:
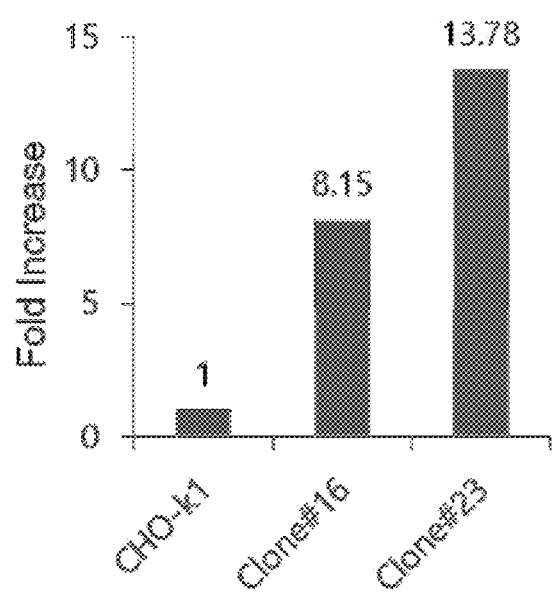
FIG. 5. CMV driven transgene expression from clones #16 and #23 compared to unmodified CHO-k1 cells. Clone#16, #23 cells, and unmodified CHO-k1 cells were transiently transfected with luciferase expression vector under the control of CMV promoter and luciferase assay was performed in duplicates 48 hours after transfection.

The result in FIG. 5 clearly shows that there is 8.15 fold and 13.78 fold increase in luciferase expression from clone #16 (VCRn16) and clone #23 (VCRn23), respectively, compared to CHO-k1 cells (KS).

Example 6

In order to further test the cells, cells were maintained in suspension culture in 50 ml bioreactors, and the characteristics of cells growth and viability of the cells were recorded for 10 days.

Figure 6:
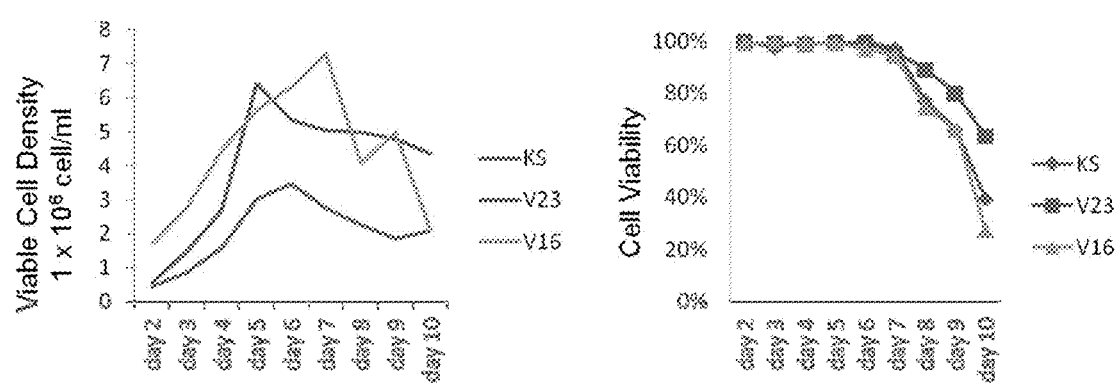
FIG. 6. Proliferative growth of Clone#16 and Clone#23 compared to the unmodified CHO-k1 cells in suspension culture. CHO-k1 (KS), Clone#16 (V16) and Clone#23 (V23) cells were grown in suspension culture in CDM4CHO medium. Cells were maintained for 10 days without feeding and cell viability and viable cell density were detected every 24 hours.

The result in FIG. 6 shows that both clones #16 (V16) and #23 (V23) grows faster and to higher densities than the original CHO-k1 cells (KS). Also, clone#23 shows an ability to maintain cell viability for longer period of time than CHO-k1 cells. Clone#23 could maintain cell viability close to 100% up to 6 days with a gradual decline after that.

Example 7

Figure 7:
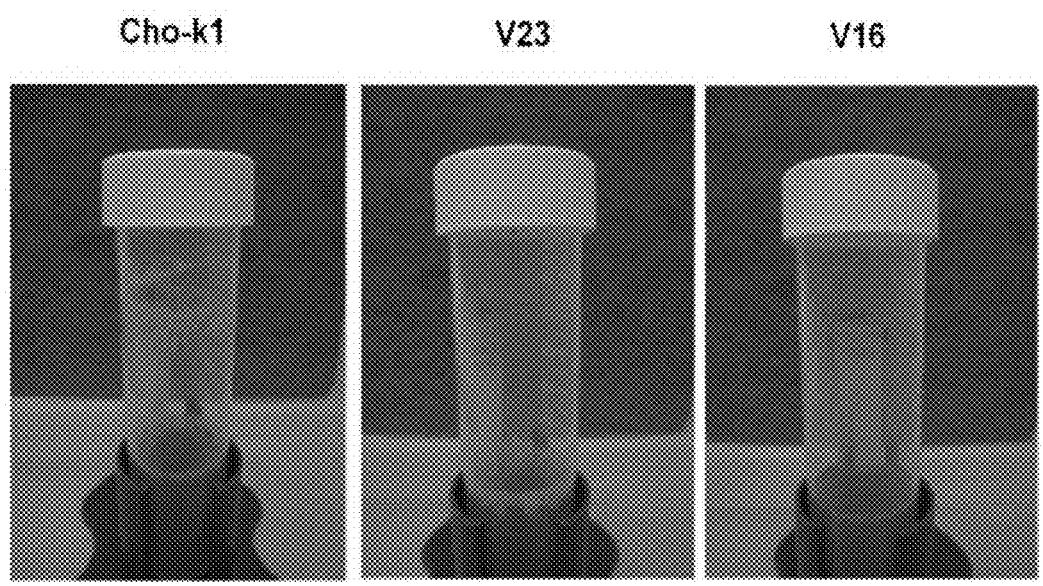
FIG. 7. Healthy growth of Clone#16 and Clone#23 compared to the unmodified CHO-k1 cells in suspension culture. CHO-k1 (KS), Clone#16 (V16) and Clone#23 (V23) cells were grown in suspension culture in CDM4CHO medium using 50 ml tubespin bioreactors and pictures were taken on day7.

Furthermore, while the original CHO-k1 cells tend to form aggregated clumps that eventually stick to the tube surface as shown in FIG. 7, both V16 and V23 cells grow without forming cell aggregation or clumps.

In summary, these two clones (V16 and V23) stably expressing VP16-CREB inside the cells can increase expression from transiently introduced genes containing CMV promoter 8-13 fold above the original CHO-k1 cells. At the same time, these clones are capable of growing faster and at higher densities and can maintain viability for longer period of time compared to the original unmodified CHO-k1 cells. Finally, these genetically modified cells have an ability to grow without forming aggregation, which can be problematic during scale-up production or during downstream processes. Generation of these clones was possible by attempting to select VP16-CREB over-expressing stable clones using an antibiotic-resistant gene selectable marker, and at the same time by selecting clones overcoming a potential apoptotic effect of CREB over-expression.

The ability of these VP16-CREB stable cells to express therapeutic proteins at high levels and to grow healthily at high densities for a long period of time in suspension culture without forming an aggregation, can add up as a significant added benefit during the industrial scale manufacturing process. It will work maximizing production efficiency and dramatically reducing overall production cost.

Example 8

Figure 8:
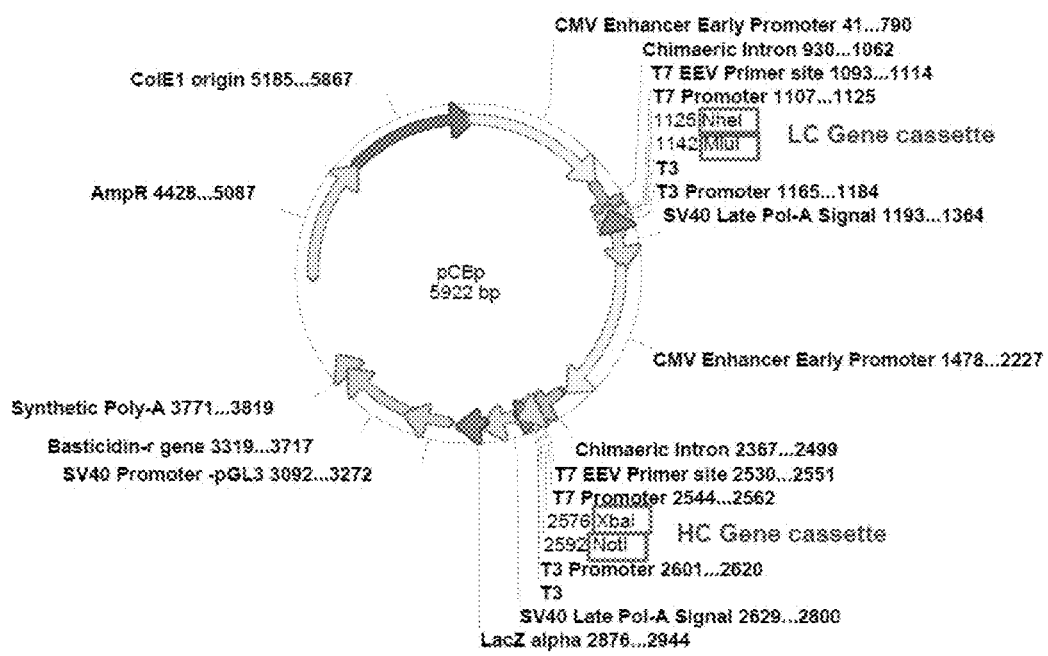
FIG. 8. pCBp2 vector map. The mammalian expression vector contains two separate expression cassettes for the expression of both the light chain and heavy chain genes of a recombinant antibody under the control of CMV promoter, along with the blasticidin-r gene to be used for antibiotic selection.
Figure 9:
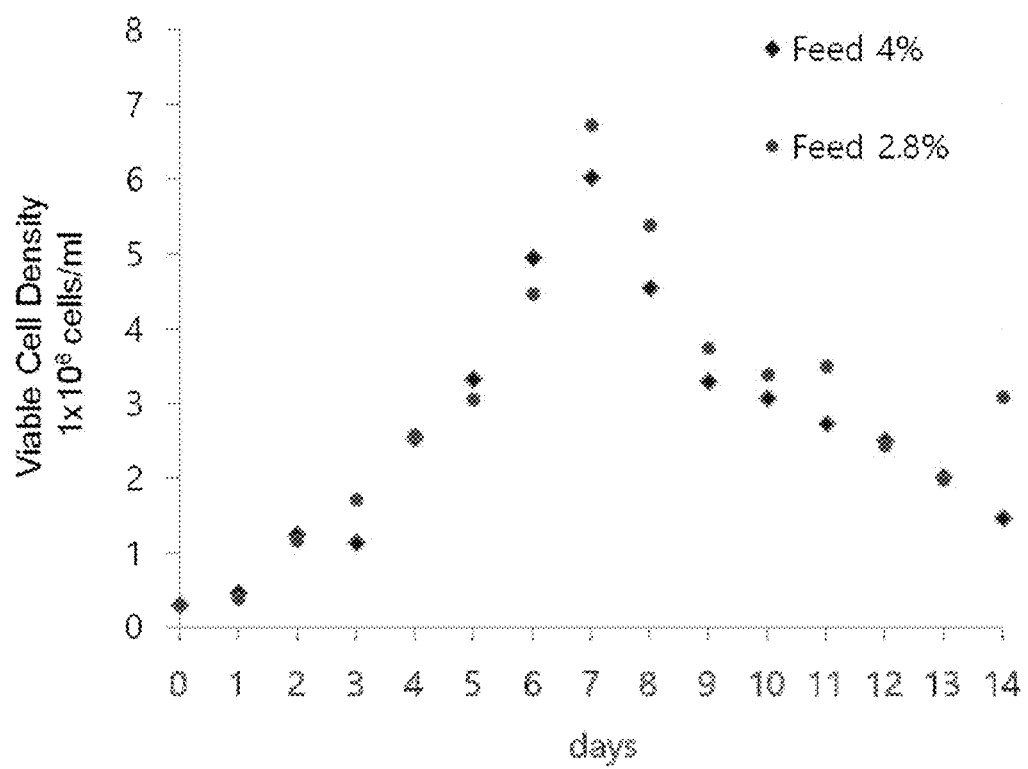
FIG. 9. Fed-batch cell growth assay for a stable cell line expressing a recombinant monoclonal antibody drug candidate developed using V23 clone as a host. Clone#e cells with 14.4 pg/cell/day specific productivity rate were grown in a 50 ml tubespin bioreactor in ActiCHO-P medium for 14 days and were fed with ActiCHO Feed-A and Feed-B in two different concentrations (4% and 2.8%) every 24 hours starting from day 3. Cell count and viability test were performed every 24 hours.
Figure 10:
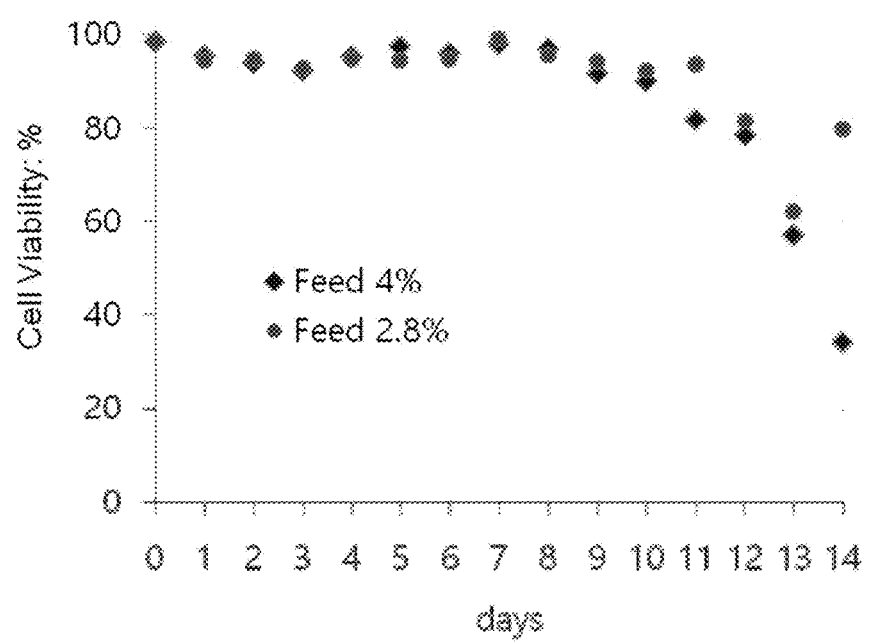
FIG. 10. Fed-batch cell viability assays for a stable cell line expressing a recombinant monoclonal antibody drug candidate developed using V23 clone as a host. Cells in FIG. 9 were tested for viability every 24 hours.
Figure 11:
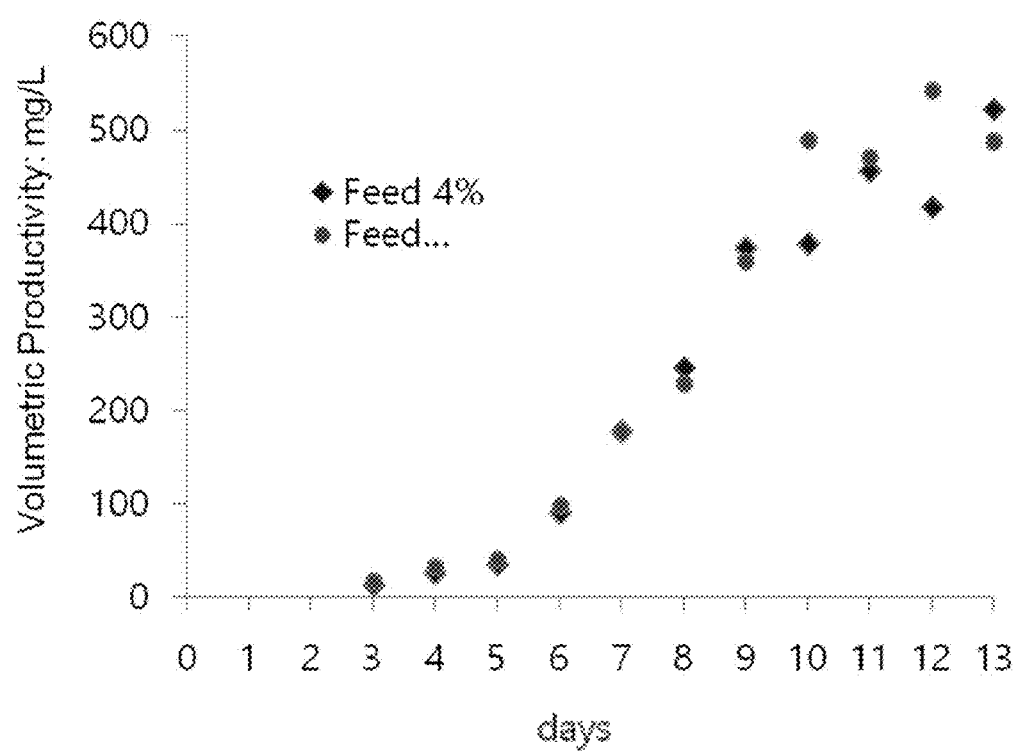
FIG. 11. Fed-batch volumetric productivity assay for a stable cell line expressing a recombinant monoclonal antibody drug candidate developed using V23 clone as a host. Cells in FIG. 9 were tested for volumetric productivity using ELISA assay using samples of the medium taken every 24 hours.

As a next step, experiments were performed to verify that these VP16-CREB over-expressing cell clones can be used as a host for the purpose of developing cell lines for the production of protein or antibody therapeutics with an increased productivity levels. Using V23 clone (named as CHO-ks1) as a host, a cell line was developed by stably transfecting the cells with a plasmid DNA (pCBp2 vector) containing expression cassettes for the heavy chain and light chain genes, respectively, of a recombinant chimeric human IgG raised against cellular target molecule, under the control of CMV promoter. See FIG. 8.

Stably transfected cells were selected using blasticidin and allowed to recover until overall cell viability reaches greater than 80%, and then FACS sorted using MoFlo-XDP cell sorter in two steps. Stably expressing cells were sorted using an R-PE conjugated antibody raised against human IgG and based on the level of R-PE fluorescence from the cells, which corresponds to the level of expression of the transfected genes. Cell sorting was performed by gating the level of R-PE fluorescence at the highest 0.1% to 1% levels, and eliminating cells expressing transgenes at low to intermediate levels.

MoFlo-XDP cell sorting was performed first into a tube as a bulk population, and after a couple of days of recovery period, into 96 well plates as single cells. Thirty to forty 96 well plates with a single cell deposited in each well were prepared for a detailed screening. Cells growing on the plates were monitored using Clone Select Imager (Molecular Devices) by scanning the image of the cells on the plate every 24 hours starting approximately 2-4 hours after the sorting of the cells into the plates. These scanned images were used later on to make sure that each of the selected clones started to grow from a single cell and not from two or more cells, verifying the clonality of the clones.

Cells on the plates were allowed to form colonies for 10-14 days and screened using a Dot Blot analysis for the level of the recombinant human IgG expression, secreted into the medium. Forty eight cell clones showing the highest levels from the Dot Blot analysis were selected and expanded into 24 well plates. Expression levels were checked again using ELISA assay and 10 of the highest expressing clones were expanded into 6 well plates, and then were used in Specific Productivity Rate (SPR) analysis.

Example 9

Determination of specific productivity rate (SPR) was performed following the method described in Brezinsky et al., "A simple method for enriching populations of transfected CHO cells for cells of higher specific productivity". *J Immunol Methods* 2003, 277:141-155.

For each population or clone, $1 \times 10^5$ cells were seeded per well of a six-well tissue culture plate (Corning) in 2-ml growth media. Assays were performed in triplicate. The cells were allowed to grow for 3 days, conditioned media harvested for analysis, and the cells were removed by centrifugation. Specific antibody titers were quantitatively determined from media samples by ELISA. The SPR measured in picograms of specific protein per cell per day (pcd) is a function of both growth rate and productivity, as represented by the following equations:

$$SPR = \frac{\text{Total protein mass}}{\text{Integral cell area } (ICA)} = qP$$

$$ICA = \frac{(\text{final cell number} - \text{initial cell number}) \times \text{days in culture}}{\log_e (\text{final cell number}/\text{initial cell number})}$$

The following table shows SPR assay result obtained from cell clones developed using CHO-ks1 (V23 clone) as a host for a recombinant human chimeric IgG antibody therapeutics candidate.

TABLE

| Clone# | assay | ug/well | F (final) | I (intial) | ICA | SPR mean pg/cell/day |
|---|---|---|---|---|---|---|
| a | 0.62 | 15.01 | 2172667 | 100000 | 2453740 | 6.14 |
| b | 0.57 | 9.63 | 922000 | 100000 | 1387654 | 6.43 |
| c | 0.72 | 18.39 | 1894333 | 100000 | 220332 | 8.29 |
| d | 0.81 | 24.88 | 1537333 | 100000 | 1915250 | 13.17 |
| e | 0.66 | 21.76 | 890000 | 100000 | 1445529 | 14.42 |

From this experiment, cell line productivity levels were recorded to be between 6.1 to 14.4 pg/cell/day. These levels were achieved without the amplification of the transfected genes, which is generally required for DG44-based cell line development for the purpose of increasing productivity levels.

Clone#e with 14.4 pg/cell/day SPR level was then expanded and used to perform a fed-batch culturing experiment to test for the volumetric productivity level, using GE's ActiCHO medium system. Cells were grown in 50 ml Tubespin Bioreactor culture vessel with a start volume of 20 ml at $3 \times 10^5$ cells/ml cell density in ActiCHO P CD medium. Cells were fed with ActiCHO Feed-A: 4% or 2.8% and ActiCHO Feed-B: 0.4% or 0.28%, respectively, following the protocol recommended by GE. Glucose levels were monitored and supplemented as the level goes below the optimum level. No other optimization except glucose supplement was performed for the experiment.

According to the result shown from the experiment, a volumetric productivity level of approximately 500 mg/L was achieved without performing process optimization of the clone generated using CHO-ks1 (V23) as the host, and in the absence of gene amplification. Gene amplification is a time consuming and frequently unstable process resulting in the loss of amplified gene copies during a scale-up manufacturing process. The ability to achieve high level of cell line productivity in the absence of gene amplification is a significant improvement over the conventional methods.

All of the references cited herein are incorporated by reference in their entirety.

REFERENCES

1. Andreatta, C. P., Nahreini, P., Hanson, A. J., and Prasad, K. N. (2004) Regulated expression of VP16CREB in neuroblastoma cells: analysis of differentiation and apoptosis. *Journal of neuroscience research* 78, 570-579
2. Barco, A., Alarcon, J. M., and Kandel, E. R. (2002) Expression of constitutively active CREB protein facilitates the late phase of long-term potentiation by enhancing synaptic capture. *Cell* 108, 689-703

3. Barco, A., Patterson, S. L., Alarcon, J. M., Gromova, P., Mata-Roig, M., Morozov, A., and Kandel, E. R. (2005) Gene expression profiling of facilitated L-LTP in VP16-CREB mice reveals that BDNF is critical for the maintenance of LTP and its synaptic capture. *Neuron* 48, 123-137

4. Bonni, A., Brunet, A., West, A. E., Datta, S. R., Takasu, M. A., and Greenberg, M. E. (1999) Cell survival promoted by the Ras-MAPK signaling pathway by transcription-dependent and -independent mechanisms. *Science* 286, 1358-1362

5. Dworet, J. H., and Meinkoth, J. L. (2006) Interference with 3',5'-cyclic adenosine monophosphate response element binding protein stimulates apoptosis through aberrant cell cycle progression and checkpoint activation. *Molecular endocrinology* 20, 1112-1120

6. Edelman, G. M., Meech, R., Owens, G. C., and Jones, F. S. (2000) Synthetic promoter elements obtained by nucleotide sequence variation and selection for activity. *Proc Natl Acad Sci USA* 97, 3038-3043

7. Eiden, L. E., Anouar, Y., Hsu, C. M., MacArthur, L., and Hahm, S. H. (1998) Transcription regulation coupled to calcium and protein kinase signaling systems through TRE- and CRE-like sequences in neuropeptide genes. *Advances in pharmacology* 42, 264-268

8. Gubbay, O., Rae, M. T., McNeilly, A. S., Donadeu, F. X., Zeleznik, A J , and Hillier, S. G. (2006) cAMP response element-binding (CREB) signalling and ovarian surface epithelial cell survival. *The Journal of endocrinology* 191, 275-285

9. Hahm, S. H., Chen, L., Patel, C., Erickson, J., Bonner, T. I., Weihe, E., Schafer, M. K., and Eiden, L. E. (1997) Upstream sequencing and functional characterization of the human cholinergic gene locus. *Journal of molecular neuroscience: MN* 9, 223-236

10. Hahm, S. H., Chen, Y., Vinson, C., and Eiden, L. E. (2003) A calcium-initiated signaling pathway propagated through calcineurin and cAMP response element-binding protein activates proenkephalin gene transcription after depolarization. *Molecular pharmacology* 64, 1503-1511

11. Hahm, S. H., and Cooper, R. H. (1992) Transforming growth factor-beta 1 rapidly activates phosphorylase in a calcium-dependent manner in rat hepatocytes. *FEBS letters* 311, 37-40

12. Hahm, S. H., and Eiden, L. E. (1996) Tissue-specific expression of the vasoactive intestinal peptide gene requires both an upstream tissue specifier element and the 5' proximal cyclic AMP-responsive element. *Journal of neurochemistry* 67, 1872-1881

13. Hahm, S. H., and Eiden, L. E. (1998) Five discrete cis-active domains direct cell type-specific transcription of the vasoactive intestinal peptide (VIP) gene. *The Journal of biological chemistry* 273, 17086-17094

14. Hahm, S. H., and Eiden, L. E. (1998) Cis-regulatory elements controlling basal and inducible VIP gene transcription. *Ann N Y Acad Sci* 865, 10-26

15. Hahm, S. H., and Eiden, L. E. (1999) Two separate cis-active elements of the vasoactive intestinal peptide gene mediate constitutive and inducible transcription by binding different sets of AP-1 proteins. *The Journal of biological chemistry* 274, 25588-25593

16. Hahm, S. H., Hsu, C. M., and Eiden, L. E. (1998) PACAP activates calcium influx-dependent and -independent pathways to couple met-enkephalin secretion and biosynthesis in chromaffin cells. *Journal of molecular neuroscience: MN* 11, 43-56

17. Hahm, S. H., Yi, Y., Lee, D. K., Noh, M. J., Yun, L., Hwang, S., and Lee, K. H. (2004) Construction of retroviral vectors with enhanced efficiency of transgene expression. *Journal of virological methods* 121, 127-136

18. Hahm, S. H., Yi, Y., Lee, D. K., Noh, M. J., Yun, L., Hwang, S., and Lee, K. H. (2004) Construction of Retroviral Vectors with Enhanced Transcription Efficiency. *J Viol Method* in press 19. Hamelink, C., Hahm, S. H., Huang, H., and Eiden, L. E. (2004) A restrictive element 1 (RE-1) in the VIP gene modulates transcription in neuronal and non-neuronal cells in collaboration with an upstream tissue specifier element. *Journal of neurochemistry* 88, 1091-1101

20. Kim, H. S., Seo, H., Yang, C., Brunet, J. F., and Kim, K. S. (1998) Noradrenergic-specific transcription of the dopamine beta-hydroxylase gene requires synergy of multiple cis-acting elements including at least two Phox2a-binding sites. *J Neurosci* 18, 8247-8260

21. Klemm, D. J., Leitner, J. W., Watson, P., Nesterova, A., Reusch, J. E., Goalstone, M. L., and Draznin, B. (2001) Insulin-induced adipocyte differentiation. Activation of CREB rescues adipogenesis from the arrest caused by inhibition of prenylation. *The Journal of biological chemistry* 276, 28430-28435

22. Klemm, D. J., Watson, P. A., Frid, M. G., Dempsey, E. C., Schaack, J., Colton, L. A., Nesterova, A., Stenmark, K. R., and Reusch, J. E. (2001) cAMP response element-binding protein content is a molecular determinant of smooth muscle cell proliferation and migration. *The Journal of biological chemistry* 276, 46132-46141

23. Lee, H. W., Hahm, S. H., Hsu, C. M., and Eiden, L. E. (1999) Pituitary adenylate cyclase-activating polypeptide regulation of vasoactive intestinal polypeptide transcription requires Ca2+ influx and activation of the serine/threonine phosphatase calcineurin. *Journal of neurochemistry* 73, 1769-1772

24. Lonze, B. E., and Ginty, D. D. (2002) Function and regulation of CREB family transcription factors in the nervous system. *Neuron* 35, 605-623

25. Lonze, B. E., Riccio, A., Cohen, S., and Ginty, D. D. (2002) Apoptosis, axonal growth defects, and degeneration of peripheral neurons in mice lacking CREB. *Neuron* 34, 371-385

26. Nahreini, P., Andreatta, C. P., Prasad, K. N., and Toribara, N. W. (2008) VP16CREB-induced differentiation of neuroblastoma. *Indian journal of pediatrics* 75, 1009-1013

27. Pugazhenthi, S., Wang, M., Pham, S., Sze, C. I., and Eckman, C. B. (2011) Downregulation of CREB expression in Alzheimer's brain and in Abeta-treated rat hippocampal neurons. *Molecular neurodegeneration* 6, 60

28. Saeki, K., Yuo, A., Suzuki, E., Yazaki, Y., and Takaku, F. (1999) Aberrant expression of cAMP-response-element-binding protein ('CREB') induces apoptosis. *The Biochemical journal* 343 Pt 1, 249-255

29. Saggioro, D. (2011) Anti-apoptotic effect of Tax: an NF-kappaB path or a CREB way? *Viruses* 3, 1001-1014

30. Sakamoto, K. M., and Frank, D. A. (2009) CREB in the pathophysiology of cancer: implications for targeting transcription factors for cancer therapy. *Clinical cancer research: an official journal of the American Association for Cancer Research* 15, 2583-2587

31. Tan, Y. W., Zhang, S. J., Hoffmann, T., and Bading, H. (2012) Increasing levels of wild-type CREB up-regulates several activity-regulated inhibitor of death (AID) genes and promotes neuronal survival. *BMC neuroscience* 13, 48

32. Xu, W., Chen, H., Du, K., Asahara, H., Tini, M., Emerson, B. M., Montminy, M., and Evans, R. M. (2001) A transcriptional switch mediated by cofactor methylation. *Science* 294, 2507-2511

33. Yu, C. T., Shih, H. M., and Lai, M. Z. (2001) Multiple signals required for cyclic AMP-responsive element binding protein (CREB) binding protein interaction induced by CD3/CD28 costimulation. *Journal of immunology* 166, 284-292

34. Zhu, D. Y., Lau, L., Liu, S. H., Wei, J. S., and Lu, Y. M. (2004) Activation of cAMP-response-element-binding protein (CREB) after focal cerebral ischemia stimulates neurogenesis in the adult dentate gyrus. *Proc Natl Acad Sci USA* 101, 9453-9457

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A V23 cell line named CHO-ks1 and deposited at the Korean Collection for Type Cultures of the Korea Research Institute of Bioscience and Biotechnology having Accession No: KCTC12810BP.

2. A method of producing a protein encoded by an exogenous transgene in a host mammalian cell, comprising transfecting the mammalian host cell according to claim 1 with an expression vector comprising a transgene, expressing the protein encoded by the exogenous transgene nucleic acid in the mammalian host cell to produce the protein.

3. The method according to claim 2, wherein the transgene is an antibody or a component of an antibody.

* * * * *